US 8,246,692 B2

(12) United States Patent
Giordano (10) Patent No.: US 8,246,692 B2
(45) Date of Patent: Aug. 21, 2012

(54) METHOD FOR TREATING A CARTILAGE DEFECT, SURGICAL INSTRUMENTATION AND SURGICAL NAVIGATION SYSTEM

(75) Inventor: Nicola Giordano, Villingen-Schwenningen (DE)

(73) Assignee: Aesculap AG, Tuttlingen (DE)

( * ) Notice: Subject to any disclaimer, the term of this patent is extended or adjusted under 35 U.S.C. 154(b) by 809 days.

(21) Appl. No.: 12/315,085

(22) Filed: Nov. 25, 2008

(65) Prior Publication Data
US 2009/0138095 A1 May 28, 2009

Related U.S. Application Data

(60) Provisional application No. 61/004,659, filed on Nov. 28, 2007.

(51) Int. Cl.
*A61F 2/02* (2006.01)
*A61B 17/29* (2006.01)
(52) U.S. Cl. ..................................... 623/23.72; 606/205
(58) Field of Classification Search .................. 606/205, 606/207; 623/23.72–23.74
See application file for complete search history.

(56) References Cited

U.S. PATENT DOCUMENTS

| 5,718,714 A | * | 2/1998 | Livneh | 606/205 |
| 5,735,873 A | * | 4/1998 | MacLean | 606/205 |
| 2006/0257379 A1 | | 11/2006 | Giordano et al. | |

FOREIGN PATENT DOCUMENTS
WO 2007/065803 6/2007

* cited by examiner

*Primary Examiner* — Ryan Severson
(74) *Attorney, Agent, or Firm* — Lipsitz & McAllister, LLC (57) ABSTRACT

The invention relates to a method for treating a cartilage defect by implanting a cartilage replacement implant through an arthroscopic access, comprising: determining at least one parameter for describing the arthroscopic access, providing a surgical instrumentation comprising at least two different applicator instruments for grasping the cartilage replacement implant, choosing one of the at least two applicator instruments of the instrumentation in dependence upon the at least one parameter determined for describing the arthroscopic access, and grasping and inserting the cartilage replacement implant into the patient's body with the chosen instrument through the arthroscopic access.

35 Claims, 5 Drawing Sheets

METHOD FOR TREATING A CARTILAGE DEFECT, SURGICAL INSTRUMENTATION AND SURGICAL NAVIGATION SYSTEM

CROSS REFERENCE TO RELATED APPLICATIONS

This application claims priority to U.S. Provisional Application No. 61/004,659 filed Nov. 28, 2007.

The present disclosure relates to the subject matter disclosed in U.S. Provisional Application No. 61/004,659 of Nov. 28, 2007, which is incorporated herein by reference in its entirety and for all purposes.

FIELD OF THE INVENTION

The present invention relates to methods for treating a cartilage defect generally, and, more specifically, to methods for treating a cartilage defect by implanting a cartilage replacement implant through an arthroscopic access.

The present invention further relates to surgical instrumentations generally, and, more specifically, to surgical instrumentations comprising at least two applicator instruments for grasping a cartilage replacement implant.

Moreover, the present invention relates to surgical navigation systems generally, and, more specifically, to surgical navigation systems comprising a detection device for wireless detection of the position and/or orientation of a palpation instrument in an operating theater.

BACKGROUND OF THE INVENTION

The present invention relates to a method for treating a cartilage defect by implanting a cartilage replacement implant through an arthroscopic access, the method comprising: providing a surgical applicator instrument for grasping the cartilage replacement implant, and grasping and inserting the cartilage replacement implant into the patient's body with the applicator instrument through the arthroscopic access.

Furthermore, the present invention relates to a surgical instrumentation comprising an applicator instrument for grasping a cartilage replacement implant, the applicator instrument having an elongate shaft and a jaw part which is arranged at the distal end portion of the shaft and is designed for grasping the cartilage replacement implant.

Moreover, the present invention relates to a surgical navigation system comprising a detection device for wireless detection of the position and/or orientation of a palpation instrument in an operating theater, the palpation instrument carrying a reference unit whose position and/or orientation in the operating theater is determinable by the navigation system. The palpation instrument is suited for insertion into a patient's body through an arthroscopic access, and the navigation system is adapted for use in treating a cartilage defect by implanting a cartilage replacement implant.

It is known in the art to treat cartilage defects using navigated arthroscopic ACT. ACT is commonly known as the abbreviation for Autologous Chondrocyte Transplantation. In a first step of the method, the cartilage defect is measured, i.e. its shape and its orientation, with navigated assistance, in particular, using a surgical navigation system of the type described above. In a next step, the detected geometry of the cartilage defect is transferred outside of the patient's body, in particular, if a cartilage defect in a patient's knee is to be treated, outside of the knee joint, to a matrix fleece which is colonized with cartilage cells. The cartilage cells are autologous cells from the patient which have been taken from the patient's body and have been grown in vitro. The fleece is then cut to size, so that the fabricated matrix fleece can be placed with an exact fit onto the cartilage defect. Procedures of the described type are known from US 2006/0257379 A1 and WO 2007/065803 A1.

Further, under arthroscopically controlled conditions, the matrix fleece is then inserted into the respective joint and positioned in the defect in order to perfectly fill it. When an arthroscopic access is used for treating the cartilage defect, the confined spatial conditions within the respective joint, for example, a knee joint of the patient, greatly impede maneuvering of the implant for placement of the implant onto the cartilage defect.

Both applications referred to relate to the detection and the transfer of defined, in particular, arthroscopically determined, cartilage defect geometries to the matrix fleece which is to be inoculated with cartilage cells and then implanted, in order that the matrix fleece can be inserted with an exact fit into the defect.

The known prior art does relate to the transfer, in particular, the arthroscopic transfer, of the cartilage defect geometry to the ACT (matrix) fleece and exact cutting thereof to size, but not to the arthroscopic application of the ACT fleece, which is difficult owing to the confined spatial conditions and the unaccustomed view.

An object underlying the present invention is, therefore, to provide a method for implanting the cartilage replacement implant onto the cartilage defect using an arthroscopic access.

SUMMARY OF THE INVENTION

In a first aspect of the invention, a method for treating a cartilage defect by implanting a cartilage replacement implant through an arthroscopic access comprises: determining at least one parameter for describing the arthroscopic access, providing a surgical instrumentation comprising at least two different applicator instruments for grasping the cartilage replacement implant, choosing one of the at least two applicator instruments of the instrumentation in dependence upon the at least one parameter determined for describing the arthroscopic access, and grasping and inserting the cartilage replacement implant into the patient's body with the chosen instrument through the arthroscopic access.

In a second aspect of the invention, a surgical instrumentation comprises at least two applicator instruments for grasping a cartilage replacement implant. Each of the at least two applicator instruments has an elongate shaft defining a longitudinal axis and a jaw part. The respective jaw part is arranged at the distal end portion of the shaft and is designed for grasping the cartilage replacement implant. A bending angle of the applicator instrument is defined between its longitudinal axis and the jaw part, wherein each of the applicator instruments having a different bending angle.

In a third aspect of the invention, a surgical navigation system comprises a detection device for wireless detection of the position and/or orientation of a palpation instrument in an operating theater. The palpation instrument carries a reference unit whose position and/or orientation in the operating theater is determinable by the navigation system. The palpation instrument is suited for insertion into a patient's body through an arthroscopic access. The navigation system is adapted for use in treating a cartilage defect by implanting a cartilage replacement implant through an arthroscopic access. The navigation system is adapted for determination of at least one parameter for describing the arthroscopic access. The navigation system is further adapted for outputting selection data which recommend to a surgeon a choice of one from at least two application instruments of a surgical instrumentation in dependence upon the at least one parameter determined for describing the arthroscopic access. The surgical instrumentation comprises at least two different applicator instruments adapted for grasping the cartilage replacement implant. Moreover, the applicator instruments are adapted for insertion into the patient's body through an arthroscopic access.

BRIEF DESCRIPTION OF THE DRAWINGS

The foregoing summary and the following description may be better understood in conjunction with the drawing figures, of which.

DETAILED DESCRIPTION OF THE INVENTION

Although the invention is illustrated and described herein with reference to the preferred embodiments, the invention is not intended to be limited to the details shown. Rather, various modifications may be made in the details within the scope and range of equivalence of the claims and without departing from the invention.

As already set forth above, the present invention relates to a method for treating a cartilage defect by implanting a cartilage replacement implant through an arthroscopic access, comprising:
determining at least one parameter for describing the arthroscopic access, providing a surgical instrumentation comprising at least two different applicator instruments for grasping the cartilage replacement implant,
choosing one of the at least two applicator instruments of the instrumentation in dependence upon the at least one parameter determined for describing the arthroscopic access, and grasping and inserting the cartilage replacement implant into the patient's body with the chosen instrument through the arthroscopic access.

The suggested method has the advantage that the best suited applicator instrument available can be used by the surgeon. This allows the surgeon to perfectly insert and place the cartilage replacement implant onto the cartilage defect without any additional maneuvering. Conventionally, the implant is inserted and placed onto the defect by means of a simple forceps. The forceps usually have two straight arms which are movable relative to each other in order to grasp and hold the implant between distal ends of the arms. The parameter for describing the arthroscopic access can be any parameter which allows a definition or description of the arthroscopic access in a spatial relationship to the cartilage defect which can also be described as cartilage defect area. The chosen applicator instrument preferably allows grasping and holding of the implant to be placed onto the defect in such a way that the applicator instrument can be inserted through the access such that the implant held by the applicator instrument is placed parallel or essentially parallel to the cartilage defect. Thus, the surgeon need not maneuver the applicator instrument relative to the patient's body which minimizes the trauma for the patient.

Preferably, a cartilage replacement ACT matrix fleece is provided for use as cartilage replacement implant. Using autologous chondrocytes for colonizing the matrix fleece has the advantage that possible rejection reactions of the body can be minimized or even excluded.

Preferably, an angle of inclination between the longitudinal axis defined by the arthroscopic access and the reference plane defined by the cartilage defect is determined for use as the at least one parameter for describing the arthroscopic access to the cartilage defect. The angle of inclination enables, in particular, if the instrumentation provided comprises applicator instruments with differently bent jaw parts or jaw portions, easy choosing of the best suited applicator instrument in dependence upon the determined angle of inclination.

Advantageously, the angle of inclination is determined using a navigated surgical instrument which is inserted into the patient's body through the arthroscopic access. For example, determining the position and the orientation of the navigated surgical instrument enables a simple and easy determination of the angle of inclination.

It is expedient for the angle of inclination to be determined using a navigated palpation instrument for palpation of the cartilage defect. The palpation instrument defines a palpation instrument axis and, preferably, is inserted through the arthroscopic access with the palpation instrument axis aligned with the longitudinal axis of the arthroscopic axis in order to determine the arthroscopic access axis and the angle of inclination. Such a simple alignment procedure also allows the surgeon to visually check the longitudinal axis of the arthroscopic access.

Moreover, it is advantageous if the angle of inclination is determined by determining the palpation instrument axis using a navigation system. In particular, this allows determining of the palpation instrument axis wirelessly. Just by holding the palpation instrument the desired parameter can be automatically determined by means of the navigation system.

Preferably, the geometry and the orientation of the cartilage defect are determined by palpating the edge of the cartilage defect with a tip of the navigated palpation instrument. This enables acquisition of data describing the cartilage defect, in particular, size, shape, position and orientation in an operating theater. The data can be used to prepare the implant to be inserted and placed onto the cartilage defect.

It is expedient if the geometry and the orientation of the cartilage defect are determined by determining the position and the orientation of the palpation instrument axis while palpating the edge of the cartilage defect using a navigation system. This improved method makes it possible for the geometry and the orientation of the cartilage defect to be automatically determined by the navigation system. In particular, it is not necessary to have a visualization system for, for example, taking a picture of the defect.

In order to ensure that the implanted cartilage replacement implant maintains its position after surgery, the cartilage replacement implant is preferably fixed to the cartilage defect.

Preferably, the cartilage replacement implant is fixed to the cartilage defect using at least one fixing element. In particular, two or more fixing elements can be used. All kinds of holding or fixing pins which can be of nail-like or screw-like design as well as surgical threads are suited as fixing elements.

It is advantageous if the instrumentation provided comprises at least two different applicator instruments for grasping the cartilage replacement implant, each of the at least two different applicator instruments having an elongate shaft and a jaw part for grasping the cartilage replacement implant, and each of the at least two applicator instruments having a different instrument angle defined between its longitudinal axis and the jaw part thereof. Such an instrumentation which can comprise two, three, four, five, six, seven, eight or even more applicator instruments allows the surgeon to choose the best suited applicator instrument for grasping and inserting the cartilage replacement implant into the patient's body.

Preferably, that instrument which has a bending angle that is closest to the determined angle of inclination is chosen from the instrumentation. This has the advantage that the implant can be held with the chosen applicator instrument with an orientation parallel or essentially parallel to a plane defined by the cartilage defect. Thus, additional maneuvering with the applicator instrument is unnecessary.

Advantageously, the cartilage replacement implant is applied to the cartilage defect using the chosen instrument. This means that with a single applicator instrument the implant can be grasped, inserted and applied to the cartilage defect.

Preferably, a grasping area which its best suited for grasping and applying the implant with the applicator instrument to the cartilage defect is determined on the implant. By determining the grasping area on the implant the implant can be grasped with the chosen applicator instrument in an advantageous manner. This means that the implant can already be grasped such that no further maneuvering of the implant for placing it onto the defect is necessary when using the applicator instrument after insertion of the applicator instrument through the arthroscopic access.

Moreover, it is expedient for an insertion instrument to be insertable into the patient's body through the arthroscopic access, the insertion instrument comprising a longitudinal channel through which the applicator instrument is inserted into the patient's body. The additional insertion instrument assists the surgeon in inserting the applicator instrument into the patient's body. Moreover, the insertion instrument helps to avoid additional trauma for the patient since the applicator instrument cannot come into contact with body tissue surrounding the arthroscopic access.

Moreover, the invention relates to a surgical instrumentation comprising at least two applicator instruments for grasping a cartilage replacement implant, each of the at least two applicator instruments having an elongate shaft defining a longitudinal axis and jaw part arranged at a distal end portion of the shaft and designed for grasping the cartilage replacement implant, wherein a bending angle of the applicator instrument is defined between its longitudinal axis and the jaw part thereof, and each of the applicator instruments has a different bending angle.

Such an instrumentation is well-suited for use in connection with the method and its preferred embodiments in accordance with the present invention described above. A surgeon can choose that applicator instrument that fits to the arthroscopic access and the physiology of the patient best, i.e. the orientation of the longitudinal axis of the arthroscopic access in relation to the cartilage defect.

Preferably, at least one of the two different applicator instruments carries a reference unit whose position and/or orientation in an operating theater is determinable using a surgical navigation system. Such an applicator instrument allows insertion of a cartilage replacement implant in a navigated manner. This means that the surgeon can be assisted by the navigation system when inserting the applicator instrument with the cartilage replacement implant into the patient's body. In particular, when the orientation and position of the cartilage defect are determined the navigation system can be designed such that it indicates to the surgeon the direction in which he has to move the applicator instrument in order to correctly place the implant on the defect.

It is advantageous for the instrumentation to further comprise a navigated palpation instrument which is insertable into a patient's body through an arthroscopic access. The navigated palpation instrument allows the surgeon in a simple and easy manner to determine, in particular, the position and the orientation of the arthroscopic access in a way which has already been described above.

To enable the determination of the orientation and position of the arthroscopic access automatically by means of a surgical navigation system, it is expedient if the palpation instrument carries a reference unit whose position and/or orientation in an operating theater are determinable using a surgical navigation system.

Preferably, the palpation instrument defines a palpation instrument axis whose position and/or orientation in an operating theater are determinable using a surgical navigation system. If the palpation instrument axis is aligned with the arthroscopic access the axis of the arthroscopic access can be automatically determined by determining the palpation instrument axis.

It is advantageous if the navigated palpation instrument has a tip for palpating the edge of the cartilage defect. Palpating the edge of the cartilage defect by moving the tip along the edge allows automatic determination of the shape, orientation and position of the cartilage defect by means of the navigation system, in particular, without taking a picture of the defect.

It is expedient if the bending angle has a value in the range of 0° to 90°. In particular, since each of the applicator instruments of the instrumentation has a different bending angle such a bending angle range allows the surgeon to choose the best-suited applicator instrument after determining, for example, the angle of inclination of the arthroscopic access in relation to a plane defined by the cartilage defect.

Preferably, at least one applicator instrument has a bending angle of 0°. This means that the jaw part extends in a distal direction and coincides with or is at least parallel to the longitudinal axis of the applicator instrument.

It is advantageous if at least one applicator instrument has a bending angle of 90°. In particular, if the arthroscopic access is oriented perpendicular to the plane defined by the cartilage defect, the implant to be applied to the defect can be moved parallel to the plane into the body and onto the defect with such an applicator instrument.

In accordance with a preferred embodiment of the invention, the bending angles of the applicator instruments forming the surgical instrumentation are 0°, 5°, 10°, 15°, 20°, 25°, 30°, 35°, 40°, 45°, 50°, 55°, 60°, 65°, 70°, 75°, 80°, 85° or 90°. Of course, other angle differences than the 5° angle differences between the bending angles of different applicator instruments can be provided if the number of the applicator instruments more or less than the number of the applicator instruments with the bending angles indicated above. The angle difference between two bending angles of different applicator instruments then depends on the number of applicator instruments forming the surgical instrumentation. Preferably, the angle differences are the same between different applicator instruments.

It is extremely easy to grasp the replacement implant if the jaw part has two clamping arms which are movable relative to each other and rest against each other in a closed position. Of course, resting against each other in a closed position means that also a spacing can be provided between the clamping arms. The spacing is preferably less than the thickness of the implant which is to be grasped by the applicator instrument.

The construction of the applicator instruments is relatively simple if the clamping arms are pivotable relative to each other. Of course, the clamping arms could also be constructed such that they are displaceable relative to each other.

Moreover, it is advantageous if the clamping arms each have a clamping surface, with the clamping surfaces facing towards each other and at least one of the clamping surfaces carrying at least one tooth. In principle, it would be sufficient if only one clamping surface carries one or more teeth, however, preferably, both clamping surfaces carry two or more teeth which allow better handling of the implant when grasped by the jaw part. Furthermore, the teeth form a simple design of the jaw part for preventing that arms from being closed completely and thereby preventing the implant held therebetween and hence the cartilage cells contained therein from being squeezed. The teeth can be designed in the form of sharp spikes or pins which perforate and, consequently, hold the implant during the closing. This holding method is significantly gentler to the cartilage cells than grasping the implant with conventional jaw parts, for example, of standard forceps. Standard forceps can usually be closed completely and have flat or substantially flat clamping surfaces.

In order to allow easy and simple maneuvering of the applicator instruments, each of the applicator instruments preferably has a handle arranged at a proximal end thereof for grasping the applicator instrument.

To enable a movement of the clamping arms relative to each other, it is advantageous if each of the applicator instruments has at least one actuating member which is coupled to at least one clamping arm in a movable manner in order to open or close the jaw part. The actuating member can be a part of the handle of the applicator instrument. If this is the case, the actuating member is preferably coupled to at least one of the clamping arms using, for instance, a push rod which is movably coupled both to the clamping arm and to the actuating member.

In order to further simplify the construction of the applicator instruments, in accordance with a preferred embodiment of the invention one of the two clamping arms is immovably or stationarily arranged on the shaft. Such a design allows a more compact construction of the jaw part of the applicator instruments.

It is expedient if the elongate shaft defines a longitudinal axis, and a bending angle of the instrument is defined between the longitudinal axis and the stationary clamping arm of the jaw part. In particular, if the second clamping arm is aligned parallel or even in contact with the stationary clamping arm, the jaw part as a whole defines a longitudinal axis when the jaw part is in the closed position.

A relative movement between the two clamping arms can be achieved in a simple constructional way if one of the two clamping arms is movably arranged on the shaft.

Grasping and holding the cartilage replacement implant is easy and gentle to the implant if the jaw part is designed in the form of a forceps. In particular, the clamping surfaces can be structured so as to improve the grasping and the holding of the implant by the forceps.

Preferably, a stop device is provided for preventing the clamping surface from directly contacting each other in a closed position of the jaw part. Such a design prevents the cartilage replacement implant, in particular, an ACT matrix fleece and the cartilage cells contained in the implant from being squeezed. The stop device can, in particular, be formed by one or more teeth carried or arranged on one or both clamping surfaces of the jaw part or by an other projection arranged on at least one of the clamping arms. The teeth keep the clamping surfaces at a defined distance from each other so as to define a spacing which is preferably slightly less in width than the thickness of the implant.

In accordance with a further preferred embodiment of the invention, the applicator instruments further comprise at least one anchor element for anchoring the jaw part to a bone or in or on the cartilage defect. In particular, the anchor element is preferably attached to the stationary jaw part or stationary clamping arm for anchoring the tip of the applicator instrument at the target position in bone or cartilage. This facilitates the holding of the instrument in position while the cartilage replacement implant is being fixed at the cartilage defect site.

In order to simplify the construction of the applicator instrument, the at least one anchor element is designed in the form of a spike.

In principle, it would be possible to insert the applicator instrument directly through the arthroscopic access into the patient's body. However, it is advantageous if the surgical instrumentation further comprises an insertion instrument which is insertable into a patient's body through the arthroscopic access and which has a channel through which the applicator instrument is insertable into the patient's body. Such an insertion instrument forms a protection for the surrounding body tissue which could come into contact with the applicator instruments if the insertion instrument were not used. Therefore, the insertion instrument assists the surgeon in minimizing trauma for the patient.

Preferably, the insertion instrument is designed in the form of an elongate sleeve defining the channel. In particular, the elongate sleeve is designed such that each of the applicator instruments of the surgical instrumentation can be moved towards the cartilage defect site through the channel of the insertion instrument. The channel can have a circular cross section. In other preferred embodiments, the cross section of the channel can be oval or rectangular.

Moreover, the present invention relates to a surgical navigation system comprising a detection device for wireless detection of the position and/or orientation of a palpation instrument in an operating theater, the palpation instrument carrying a reference unit whose position and/or orientation in the operating theater is determinable by the navigation system, the palpation instrument being suited for insertion into a patient's body through an arthroscopic access, the navigation system being adapted for use in treating a cartilage defect by implanting a cartilage replacement implant through an arthroscopic access, the surgical navigation system being adapted for determination of at least one parameter for describing the arthroscopic access, the navigation system being further adapted for outputting selection data which recommends to a surgeon a choice from at least two applicator instruments of a surgical instrumentation in dependence upon the at least one parameter determined for describing the arthroscopic access, the surgical instrumentation comprising at least two different applicator instruments adapted for grasping the cartilage replacement implant.

Such an improved surgical navigation system allows a surgeon to determine the at least one parameter for describing the arthroscopic access automatically. Moreover, after this parameter is determined, the navigation system is further adapted to make a recommendation to the surgeon as to which of the at least two applicator instruments should be used for inserting the cartilage replacement implant into the patient's body and to the cartilage defect site. Although it is recommended that the surgeon controls or checks the selection data provided by the surgical navigation system, the system accelerates the procedure since determining and recommending the preferred applicator instrument by the navigation system is considerably faster than a comparable procedure performed by the surgeon himself.

The method according to the invention as well as the surgical instrumentation and the surgical navigation system according to the invention described above will be explained in greater detail in the following in conjunction with FIGS. 1 to 7 on the basis of a preferred embodiment. Moreover, more details of the methods are described in U.S. provisional application No. 61/004,659 which is again herein incorporated by reference in its entirety and for all purposes.

Figure 1:
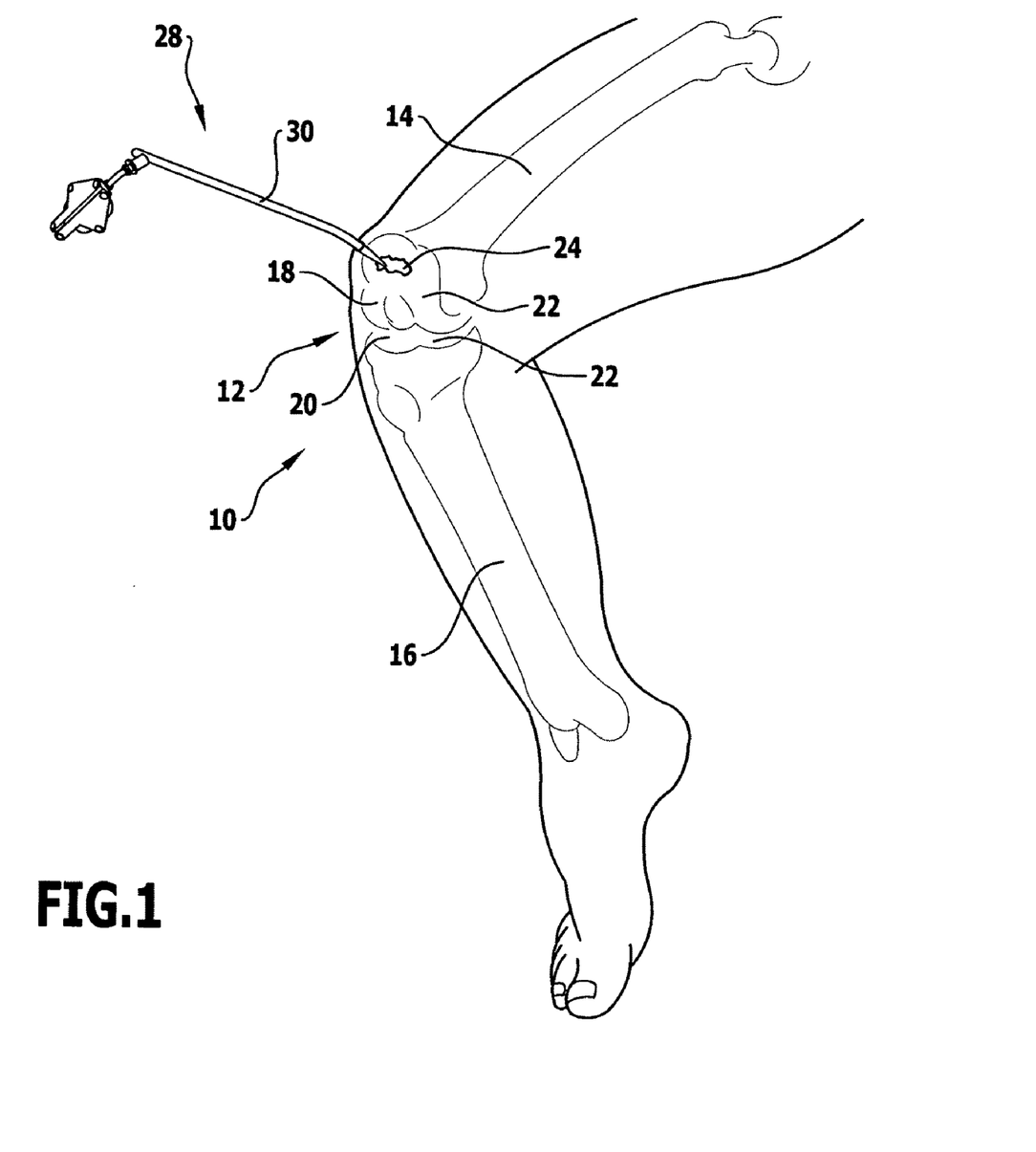
FIG. 1: shows a schematic view of a patient's leg while determining the size and/or orientation of a cartilage defect in the knee joint using a navigated palpation instrument.

In FIG. 1 a leg 10 of a human being is schematically shown with a knee joint 12 defined between a femur 14 and a tibia 16. The joint surfaces 18 and 20 of the femur 14 and the tibia 16 are both covered with cartilage tissue 22.

A cartilage defect 24 can, in particular, result from an injury, for example, a sports injury. Typically, the cartilage tissue 22 shows an area where the cartilage tissue is destroyed or partly removed due to the injury.

The present invention enables treatment of the cartilage defect 24 through an arthroscopic access 26. The arthroscopic access 26 is usually made by a small incision in the soft tissue in order to define an access channel through the body's soft tissue and thereby provide an access to the cartilage defect 24 for surgical instruments of a surgical instrumentation.

A navigated palpation instrument 28 is used to determine the geometry, position and/or orientation of the cartilage defect 24. The navigated palpation instrument 28 comprises an elongate shaft 30 defining a longitudinal axis 32 and has a tip 34 at its distal end which can be used for palpating an edge 36 of the cartilage defect 24.

The navigated palpation instrument 28 carries a reference unit 38 comprising at least three reference elements 40. The reference elements 40 can be of the active or passive type. Active-type reference elements 40 are adapted for transmitting electromagnetic radiation to a navigation system given the overall reference 42. The navigation system 42 has a transmitting and receiving station 44 which is controlled by a computer 46 used as a data processing unit and comprises several transmitting and receiving units 48 for transmitting and receiving electromagnetic radiation both in the visible and in the infrared range or ultrasound which is emitted or reflected by passive reference elements 40. The navigation system 42 additionally comprises a display device 50 in the form of a screen as well as an input device in the form of a keyboard 52. In order to increase the efficiency of the system further, computing units can co-operate with the computer 46. To ensure the functioning of the navigation system 42 in an optimum manner, at least two, preferably three, spatially separated transmitting and receiving units 48 are provided.

The navigation system 42 is adapted to determine the position and/or orientation of the reference unit 38 in an operating theater in which the surgical procedure is performed. Since the reference unit 38 is arranged in an unambiguous manner on the shaft 30 at a proximal end thereof, the navigation system 42 can also determine the longitudinal axis 32 of the shaft 30 automatically and in real time.

Figure 2:
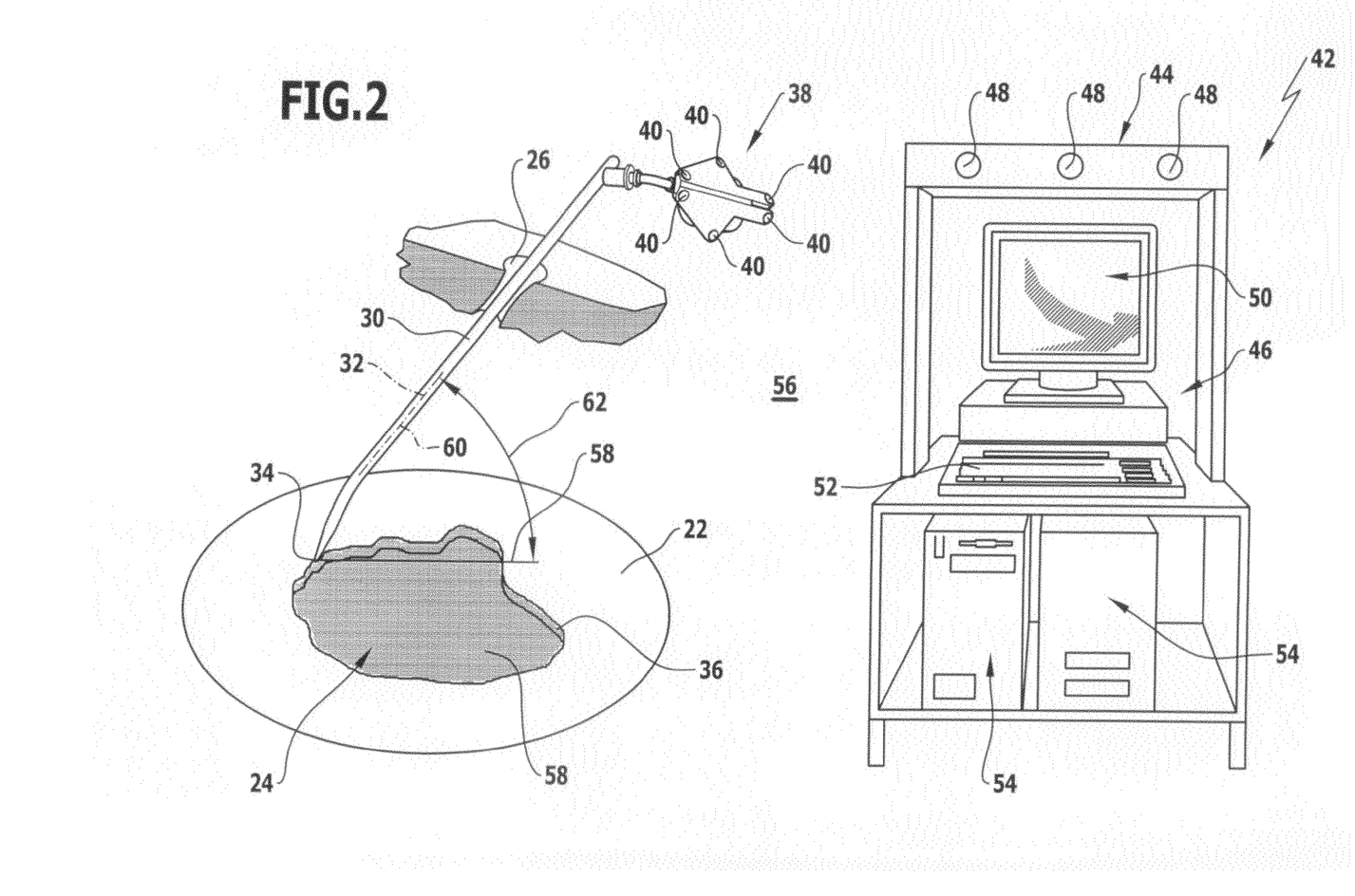
FIG. 2: shows a schematic perspective view of determining an angle of inclination of the arthroscopic access relative to a reference plane defined by the cartilage defect using a navigated palpation instrument.

After the incision is made for opening the arthroscopic access 26, the palpation instrument 28 can be introduced through the access 26 in order to palpate the edge 36 for determining the size, contour, orientation and position of the cartilage defect 24 in the operating theater 26 with the assistance of the navigation system 42. The cartilage defect 24 defines a reference plane 58 in relation to which the arthroscopic access 26 with its axis 60 is usually inclined through an angle of inclination 62 in the range of 0° to 90°.

In order to determine the axis 60 automatically, the shaft 30 is aligned with the axis 60 of the arthroscopic access 26 so that the axis 60 coincides with the longitudinal axis 32. Since the reference plane 58 is automatically determined using the navigation system 42 the angle of inclination 62 can be calculated automatically when the position and orientation of the axis 60 are known. As described, the axis 60 can also be determined automatically by the navigation system 42. The cartilage defect data determined by the navigation system 42 are used for preparing a cartilage replacement implant 64 in the form of an ACT matrix fleece colonized with autologous cartilage cells of the patient. The implant 64 has a size and a shape which perfectly fit the cartilage defect 24.

Figure 3:
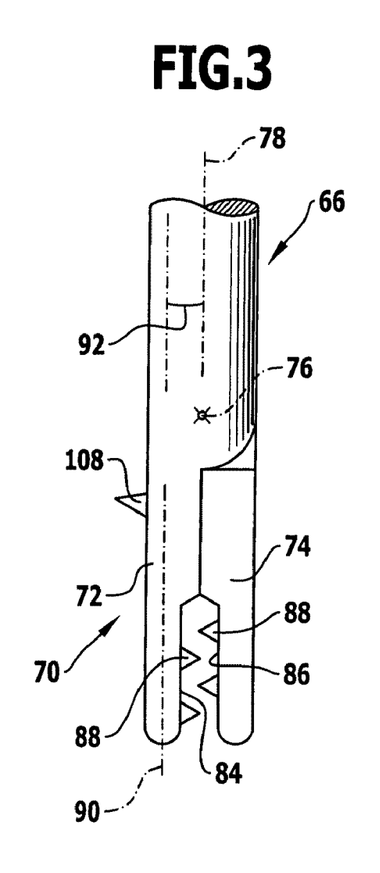
FIG. 3: shows a distal end of a first embodiment of an applicator instrument of a surgical instrumentation in accordance with the present invention.
Figure 4:
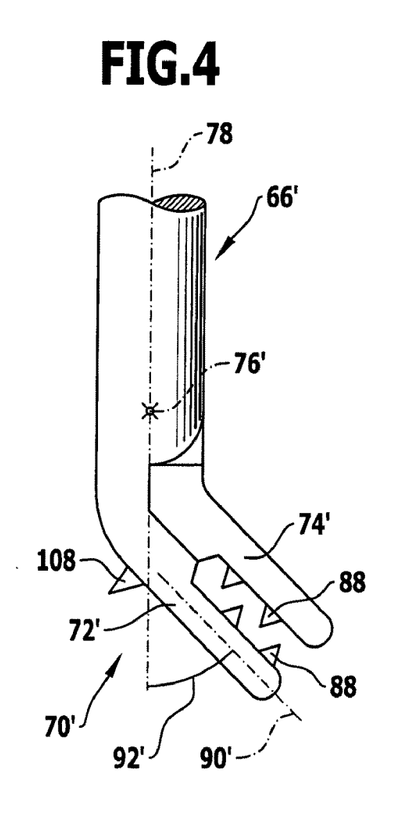
FIG. 4: shows a distal end of a second embodiment of an applicator instrument of the surgical instrumentation in accordance with the present invention.
Figure 5:
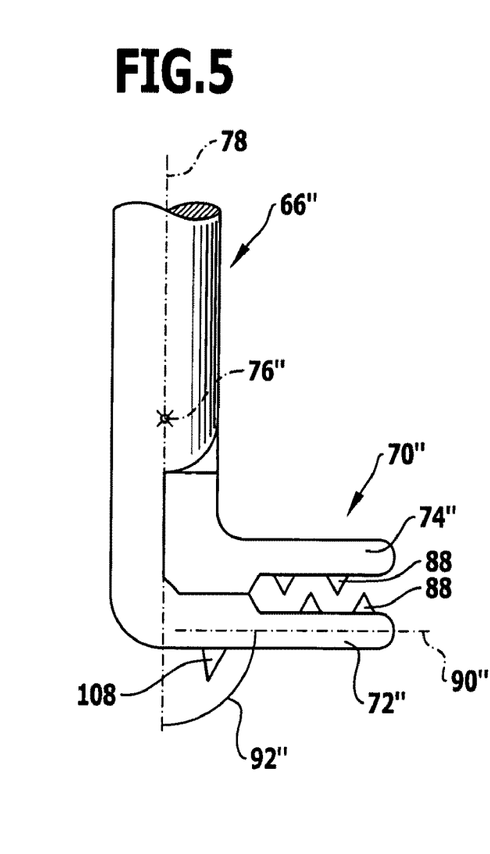
FIG. 5: shows a distal end of a third embodiment of an applicator instrument of the surgical instrumentation in accordance with the present invention.

For inserting the implant 64 through the arthroscopic access 26 and for placing it on the cartilage defect 24, the surgical instrumentation further provides two or more applicator instruments 66. Each of the applicator instruments 66 has an elongate shaft 68. Arranged at a distal end of the shaft 68 is a jaw part 70 which comprises two clamping arms 72 and 74. The clamping arm 72 is immovably or stationarily arranged on the shaft 68. The other clamping arm 74 is movable relative to the clamping arm 72, in particular, it is pivotable about a pivot axis 76 which is oriented perpendicular to the longitudinal axis defined by the shaft 68.

In addition, the jaw part 70 can have one or more anchor elements 108 in the form of a projection, for example, in the form of a spike or a double spike or the like with which the instrument 66 can be easily anchored in the bone or on the cartilage tissue 22 in order that an operator will not slip off when the matrix fleece forming the cartilage replacement implant 64 is held in position until its final fixing with special fixing elements, for example, pins or a surgical thread.

A handle 80 is arranged at a proximal end of the shaft 68 and comprises an actuating member 82 which is movably coupled with the movable clamping arm 74. In particular, the actuating member 82 is pivotably secured to the handle 80 about a pivot axis, not shown in the drawings, which is preferably parallel to the pivot axis 76. Pivoting the actuating manner 82 results in a movement of the clamping arm 74 relative to the clamping arm 72 in order to open and close the jaw part 70.

Clamping surfaces 84 and 86 of the clamping arms 72 and 74 carry teeth 88 in the form of sharp projections pointing towards the respective other clamping surface 84 and 86. In a closed position of the jaw part 70, as shown in FIGS. 3 to 5, the clamping surfaces 84 and 86 are at a distance from each other. The height of the teeth 88 is slightly less than the distance between the clamping surfaces 84 and 86 in the closed position of the jaw part 70.

The applicator instruments 66 of the surgical instrumentation differ in the design of the jaw part 70. With reference to FIGS. 3 to 5, a longitudinal axis 90 of the stationary clamping arm 72 and the longitudinal axis 78 of the shaft 68 define a bending angle 92 therebetween.

If the axis 90 is parallel to the longitudinal axis 78, the bending angle 92 is 0° as shown in FIG. 3. A jaw part 70' of an applicator instrument 66' having a bending angle 92' of 45° is shown in FIG. 4. A jaw part 70" of an applicator instrument 66" defining a bending angle 92" of 90° is shown in FIG. 5.

Figure 6:
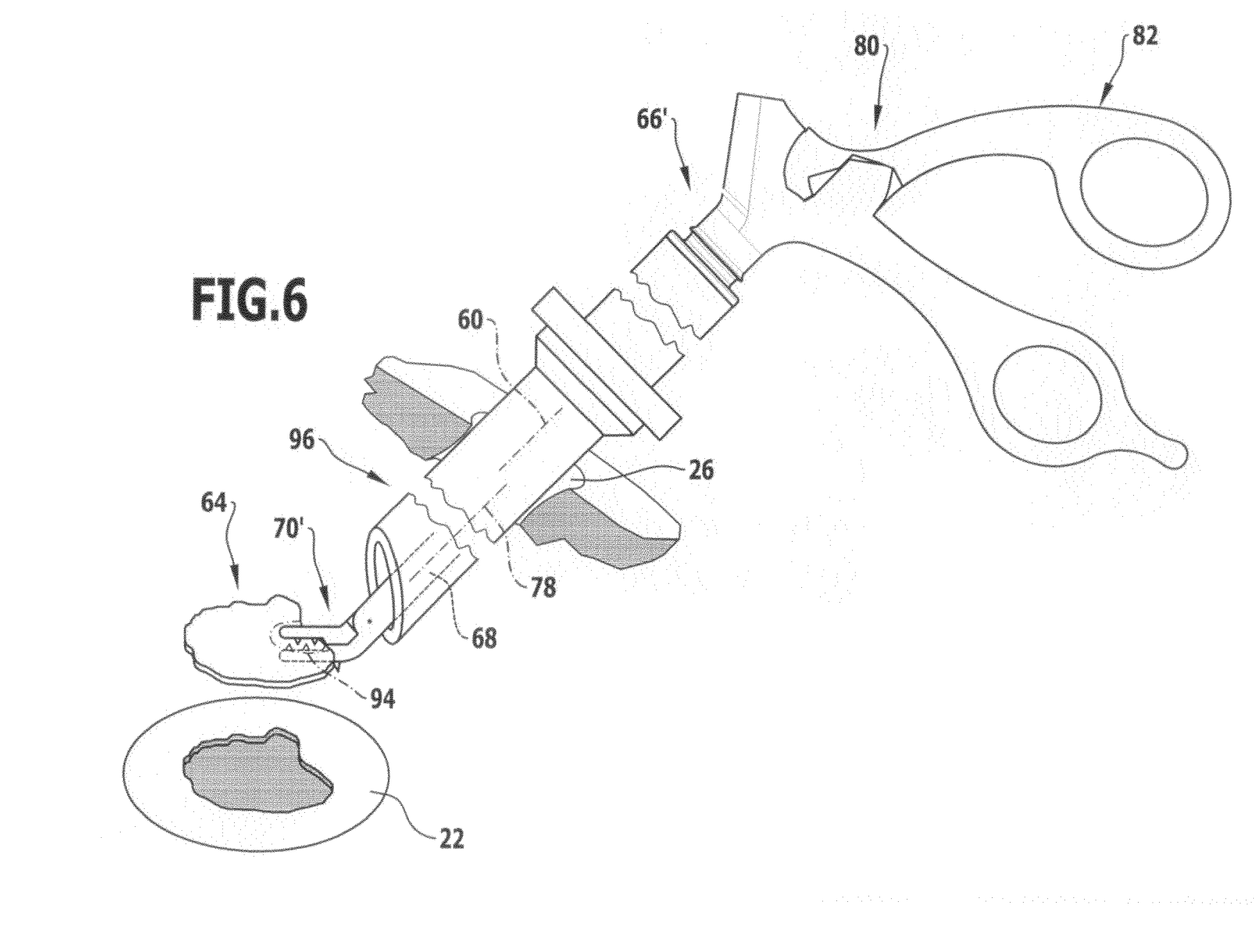
FIG. 6: shows a schematic perspective view of a surgical site while inserting a cartilage replacement implant using an applicator instrument and an insertion instrument of the surgical instrumentation in accordance with the present invention.

The applicator instruments 66 allow grasping and holding of the cartilage replacement implant 64 with their jaw parts 70 of forceps-like construction between the clamping arms 72 and 74 as illustrated in FIG. 6.

The bending angles 92 of the applicator instruments 66 are in a angle range of 0° to 90°, which corresponds to the possible angles of inclination 62 which can be in the range of 0° to 90°.

In order to minimize a maneuvering of the cartilage replacement implant inside the body for placing it correctly on the cartilage defect 24, the navigation system 42 recommends to the surgeon the best suited applicator instrument 66 of the surgical instrumentation for grasping and inserting the cartilage replacement implant 66. In the example shown in FIGS. 1 to 6, the angle of inclination 62 is about 50°. The navigation system 42 determines automatically the bending angle 92 of the three applicator instruments 66 that is closest to the determined angle of inclination 62. With reference to the drawings, the applicator instrument 66' having a bending angle 92' of 45° is closest, so that this applicator instrument 66' is recommended by the navigation system 42 for use for grasping and inserting the cartilage replacement implant 64 through the arthroscopic access 26 into the patient's body. Selection data output by the navigation system 42 can be, for example, an instrument number of the instrumentation or a color related to the determined bending angle 92 or the angle of inclination 62.

As described above, the number of applicator instruments can be even higher than the three shown in the drawings. However, the applicator instruments differ from each other with respect to the bending angles 92 of their jaw parts 70.

Choosing an applicator instrument 66 in the described manner enables placement of the cartilage replacement implant 64 parallel or almost parallel onto the cartilage defect 24. Moreover, if the orientation of the arthroscopic access 26 relative to the cartilage defect 24 is determined, the navigation system 42 can optionally also indicate a grasping area 94 defined on the cartilage replacement implant 64, which allows the surgeon to grasp the implant 64 at the grasping area 94 in order to avoid excessive maneuvering of the applicator instrument 66, in particular, turning it around the longitudinal axis 78. Thus, it is possible to place the cartilage replacement implant 64 with an optimum fit onto the cartilage defect 24.

Figure 7:
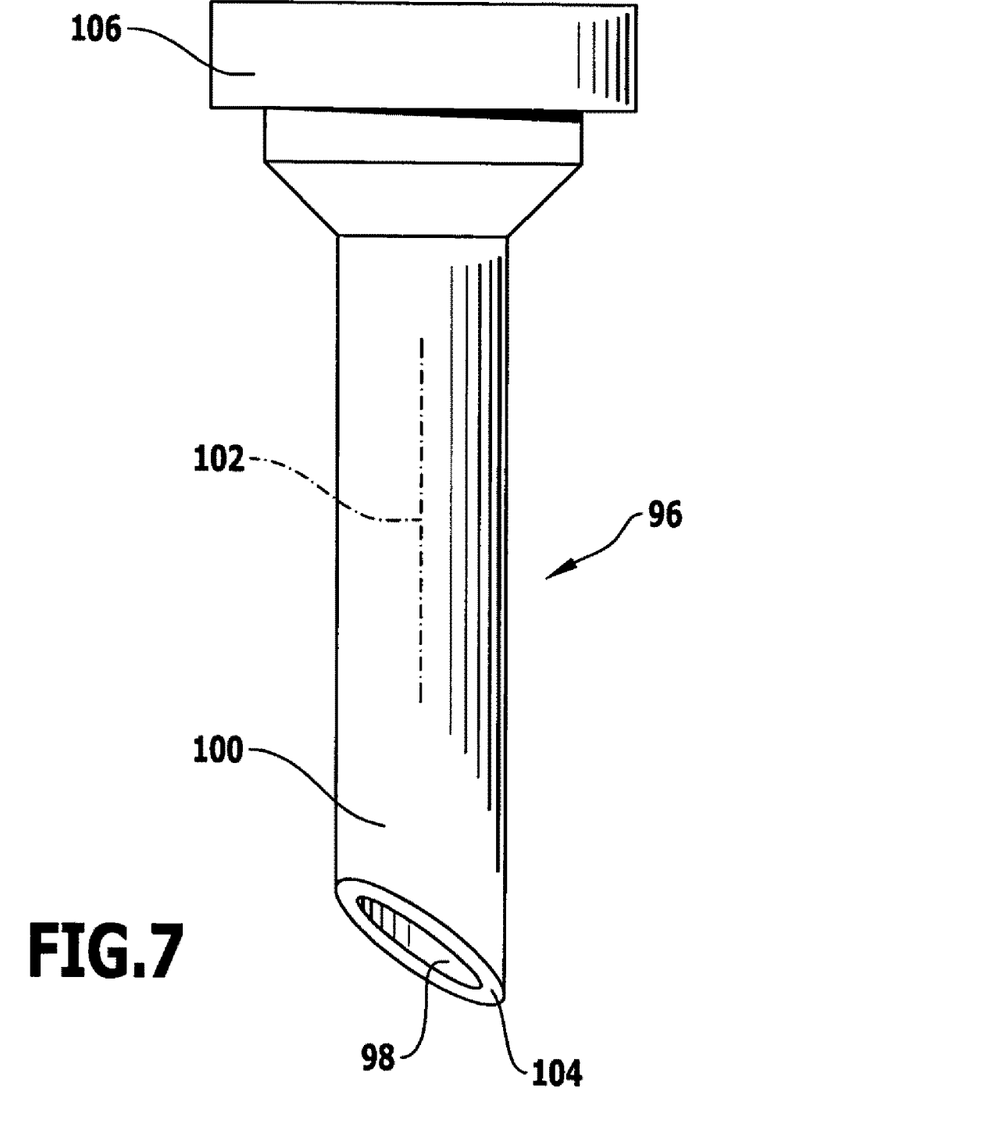
FIG. 7: shows a perspective view of the insertion instrument of the surgical instrumentation in accordance with the present invention.

The surgical instrumentation further comprises an optional insertion instrument 96 defining a longitudinal channel 98 through which all of the applicator instruments 66 can be introduced. The insertion instrument 96 comprises an elongate sleeve 100 defining a longitudinal axis 102. A distal end of the sleeve 100 is tapered at an angle of approximately 45° relative to the axis 102. The sleeve 100 forms a rim 104 surrounding the distal end of the channel 98. Arranged at a proximal end of the sleeve 100 is a holding ring 106 which can be held either by the surgeon's hand or by a holding device of the operating theater 56, not shown in the drawings.

The insertion instrument 96 is preferably used for protecting the body tissue surrounding the opened arthroscopic access 26 in order to avoid further trauma for the patient when the applicator instruments 66 are inserted. Therefore, after opening the arthroscopic access 26 the insertion instrument 96 is preferably introduced so as to define an operating channel simplifying introduction of the applicator instruments 66.

The surgical instrumentation described as well as the method for implanting an ACT matrix fleece are briefly summarized below.

The present invention relates to a surgical instrumentarium, in particular, to an ACT matrix applicator instrumentarium for navigated ACT.

The following issues are some of the underlying problems to be solved by the invention. In navigated arthroscopic ACT a cartilage defect is measured with navigated assistance. The detected geometry of the cartilage defect is then transferred outside of the knee joint to a matrix fleece colonized with cartilage cells, which is cut to size, so that the fabricated matrix fleece can be placed with an exact fit onto the cartilage defect.

Under arthroscopically controlled conditions, the matrix fleece is then inserted into the knee joint, positioned and fixed with resorbable pins.

The procedure is by way of example visualized in the "Results of the Validation Study—CDM Module V2.0 with the OrthoPilot®" forming part of U.S. provisional patent application No. 61/004,659.

When the arthroscopic procedure is used, the confined spatial conditions within the knee joint greatly impede maneuvering of the matrix fleece for placement of the matrix fleece onto the cartilage defect.

Known prior art are the publications US 2006/0257379 A1 and WO 2007/065803 A1. Both patent applications relate to the detection and the transfer of defined, in particular, arthroscopically determined, cartilage defect geometries to the matrix fleece which is to be inoculated with cartilage cells and then implanted, in order that the matrix fleece can be inserted with an exact fit into the defect. This transfer of the cartilage defect geometry to the matrix fleece is the starting point of the present invention.

The prior art does describe the transfer, in particular, the arthroscopic transfer, of the cartilage defect geometry to the ACT (matrix) fleece and the exact cutting thereof to size, but not the arthroscopic application of the ACT fleece, which is difficult owing to the confined spatial conditions and the unaccustomed view.

One of the objects of this invention is to so design an applicator instrumentarium, also with the option of navigated assistance, that there is hardly any need for maneuvering the matrix fleece in the knee joint in order, on the one hand, to insert it with an exact fit into the cartilage defect, and, on the other hand, to securely hold it in position there, i.e., in particular, "in a slip-free manner", until it is secured, in particular, fixed with holding pins.

A brief description of how some of the objects are accomplished by the invention is outlined below.

During the navigated palpation of the cartilage defect with a palpation instrument, a so-called pointer, not only the geometry of the defect is determined, as is known from the prior art, but now also the orientation of the cartilage defect relative to the selected arthroscopic access, namely:

the angular position in relation to the pointer axis and (optional)

the edge of the cartilage defect that is most convenient to reach with the pointer tip.

The navigation system then determines in dependence upon the detected angular position, i.e., in dependence, in particular, upon an angle between a straight line intersecting the cartilage defect perpendicularly and a longitudinal axis defined by the pointer, the suitable applicator instrument, with straight jaw parts, i.e., pointing in the longitudinal direction of the pointer, and extending at an angle of 45° to the longitudinal axis or at an angle of 90° in relation to the longitudinal axis, for this arthroscopic access, so that the matrix fleece can be inserted without any difficulty into the cartilage defect with this instrument. Optionally, further instruments with an angle between the jaw part axes, preferably when the jaw parts are closed, and the longitudinal axis of the instrument are also conceivable, namely, in particular, angles of 10°, 15°, 20°, 25°, 30°, 35°, 40°, 50°, 55°, 60°, 65°, 70°, 75°, 80° and 85°. The respective instrument is determined by minimizing a deviation between the angular position determined with the pointer and the angles of inclination of the jaw parts of the available instruments.

When transferring the cartilage defect geometry to the matrix fleece, it can be additionally indicated where exactly the matrix fleece must be held with the forceps in order that, after insertion into the knee joint, it can be placed onto the cartilage defect without any maneuvering.

The jaw parts of the applicator instruments, which are preferably in the form of forceps, expediently have long pointed teeth, in order that, on the one hand, the matrix fleece can be held securely, and, on the other hand, the jaw parts, also referred to as jaw arms, can be prevented from being closed completely, in order that the sensitive cartilage cells, with which the fleece was inoculated, do not get squeezed.

Preferably, one of the jaw parts of the applicator instruments of the instrumentarium is stationary relative to a shaft of the respective instrument. The angles between jaw part and longitudinal axis stated hereinabove then preferably relate to the stationary jaw part.

In addition, the stationary jaw part may optionally comprise an "anchor" in the form of a projection, for example, in the form of a spike or a double spike or the like, with which the instrument can be easily anchored in the bone or in or on the cartilage, in order that an operator will not slip off when the matrix fleece is held in position until the final fixing with pins.

Optionally, in order to introduce the matrix fleece gently into the knee joint, an applicator sleeve of the instrumentarium, for example, in the form of an applicator tube, which may have an oblique distal end, is first pushed onto the forceps selected in accordance with the respective operating situation. The matrix fleece is then grasped at the optionally determined, correct and optionally marked place and drawn into the applicator sleeve. The applicator sleeve is subsequently introduced through the arthroscopic access opened on the patient's body, and the matrix fleece is pushed out of the applicator sleeve. Owing to the suitably selected instrument and the suitably selected place for grasping, the matrix fleece can be immediately placed with an exact fit onto the cartilage defect site without any maneuvering.

The novelty of this solution according to the invention is briefly described below.

Both the entire method of navigated arthroscopic ACT set forth hereinabove and the instrumentarium proposed therefor are novel, i.e., in particular, the extraarticular fabrication of the ACL matrix fleece and the determination of the appropriate instrument of the available instrumentarium, so as to enable intraarticular insertion of the fleece arthroscopically without maneuvering to any great extent.

Innovations in the software and navigation fields are:
a) The determination of the access parameters in accordance with the selected arthroscopic access and, in conclusion therefrom, determination of the suitable offset, i.e., for example, the bend of a stationary jaw part relative to a longitudinal axis of the instrument, on the instrument or of a longitudinal axis of the arthroscopic operation access for insertion of the ACT matrix fleece.
b) The determination of the suitable place for grasping the ACT matrix fleece with the forceps in accordance with the selected arthroscopic access, in order that the ACT matrix fleece can be placed onto the defect site without any further intraarticular maneuvering.

Innovations in the instrument field are:
a) The jaw parts of the forceps bent at different angles are designed so that the arms are unable to be closed completely so as to prevent the ACT matrix fleece and hence the cartilage cells therein from being squeezed. In order to nevertheless hold the ACT matrix fleece firmly and securely, sharp spikes which perforate and, consequently, hold the ACT matrix fleece during the closing are provided on one or both jaw parts. This holding method is significantly gentler on the cartilage cells than grasping with conventional jaw parts, which can be closed completely and usually have flat or substantially flat clamping surfaces.
b) An anchoring spike is preferably attached to the stationary jaw part for anchoring the tip of the instrument at the target position in bone or cartilage. This facilitates the holding of the instrument in position while the ACT matrix fleece is being fixed at the cartilage defect site.
c) In its diameter, the applicator sleeve is preferably adapted to the applicator forceps so as to enable the ACT matrix fleece to be drawn into the applicator sleeve and brought into the knee interior in a manner which is gentle on the cartilage cells.

Some of the advantages resulting from this invention are listed below:
the possibility of arthroscopic ACT implantation
the avoidance of intraarticular maneuvering during the ACT implantation
the holding and introducing of the ACT matrix fleece in a manner which is gentle on the cartilage cells
the anchoring the grasping instrument at the target location for positioning the ACT matrix fleece with ease while it is being fixed at the cartilage defect site.

What is claimed is:

1. A method for treating a cartilage defect by implanting a cartilage replacement implant through an arthroscopic access, comprising:
determining at least one parameter for describing the arthroscopic access,
providing a surgical instrumentation comprising at least two different applicator instruments for grasping the cartilage replacement implant,
choosing one of the at least two applicator instruments of the instrumentation in dependence upon the at least one parameter determined for describing the arthroscopic access, and
grasping and inserting the cartilage replacement implant into a patient's body with the chosen instrument through the arthroscopic access,
wherein:
each of the at least two different applicator instruments has an elongate shaft defining a longitudinal axis and a jaw part for grasping the cartilage replacement implant,
each of the at least two applicator instruments has a different bending angle defined between the longitudinal axis and the jaw part, and
the applicator instrument which has a bending angle that is closest to a determined angle of inclination is chosen from the instrumentation.

2. A method according to claim 1, wherein a cartilage replacement ACT matrix fleece is provided for use as cartilage replacement implant.

3. A method according to claim 1, wherein:
the determined angle of inclination comprises an angle between a longitudinal axis defined by the arthroscopic access and a reference plane defined by the cartilage defect, and
the determined angle of inclination is used as the at least one parameter for describing the arthroscopic access to the cartilage defect.

4. A method according to claim 3, wherein the angle of inclination is determined using a navigated surgical instrument which is inserted into the patient's body through the arthroscopic access.

5. A method according to claim 3, wherein the angle of inclination is determined using a navigated palpation instrument for palpation of the cartilage defect, which defines a palpation instrument axis, the palpation instrument is inserted through the arthroscopic access with the palpation instrument axis aligned with the longitudinal axis of the arthroscopic access in order to determine the longitudinal axis of the arthroscopic access.

6. A method according to claim 5, wherein the angle of inclination is determined by determining the palpation instrument axis using a navigation system.

7. A method according to claim 5, wherein a geometry and an orientation of the cartilage defect are determined by palpating an edge of the cartilage defect with a tip of the navigated palpation instrument.

8. A method according to claim 7, wherein the geometry and the orientation of the cartilage defect are determined by determining a position and an orientation of the palpation instrument axis while palpating the edge of the cartilage defect using a navigation system.

9. A method according to claim 1, wherein the cartilage replacement implant is fixed to the cartilage defect.

10. A method according to claim 9, wherein the cartilage replacement implant is fixed to the cartilage defect using at least one fixing element.

11. A method according to claim 1, wherein the cartilage replacement implant is applied to the cartilage defect using the chosen applicator instrument.

12. A method according to claim 1, wherein a grasping area which is best suited for grasping and applying the implant with the applicator instrument to the cartilage defect is determined on the implant.

13. A method according to claim 1, wherein an insertion instrument is insertable into the patient's body through the arthroscopic access, the insertion instrument comprising a longitudinal channel through which the applicator instrument is inserted into the patient's body.

14. A surgical navigation system, comprising:
a detection device for wireless detection of at least one of a position and orientation of a palpation instrument in an operating theater,
said palpation instrument carrying a reference unit, at least one of a position and orientation of the reference unit in the operating theater is determinable by the navigation system,
said palpation instrument being suited for insertion into a patient's body through an arthroscopic access,
said surgical navigation system being adapted for use in treating a cartilage defect by implanting a cartilage replacement implant through the arthroscopic access,
said surgical navigation system being adapted for determination of at least one parameter for describing the arthroscopic access,
said surgical navigation system being further adapted for outputting selection data which recommend to a surgeon a choice of one from at least two applicator instruments of a surgical instrumentation in dependence upon the at least one parameter determined for describing the arthroscopic access, and
said surgical instrumentation comprising at least two different applicator instruments adapted for grasping the cartilage replacement implant,
wherein:
each of the at least two different applicator instruments has an elongate shaft defining a longitudinal axis and a jaw part for grasping the cartilage replacement implant,
each of the at least two applicator instruments has a different bending angle defined between the longitudinal axis and the jaw part, and
the selection data recommends the applicator instrument which has a bending angle that is closest to a determined angle of inclination for use in implanting the cartilage replacement implant through the arthroscopic access.

15. A surgical navigation system according to claim 14, wherein at least one of the at least two different applicator instruments carries a reference unit whose position and/or orientation in an operating theater is determinable using the surgical navigation system.

16. A surgical navigation system according to claim 14, wherein the palpation instrument defines a palpation instrument axis whose position and/or orientation in an operating theater are determinable using a surgical navigation system.

17. A surgical navigation system according to claim 14, wherein the navigated palpation instrument has a tip for palpating an edge of the cartilage defect.

18. A surgical navigation system according to claim 14, wherein the bending angle has a value in a range from 0° to 90°.

19. A surgical navigation system according to claim 14, wherein at least one of the at least two applicator instruments has a bending angle of 0°.

20. A surgical navigation system according to claim 14, wherein at least one of the at least two applicator instruments has a bending angle of 90°.

21. A surgical navigation system according to claim 14, wherein the bending angles are 0°, 5°, 10°, 15°, 20°, 25°, 30°, 35°, 40°, 45°, 50°, 55°, 60°, 65°, 70°, 75°, 80°, 85° or 90°.

22. A surgical navigation system according to claim 14, wherein the jaw part has two clamping arms which are movable relative to each other and rest against each other in a closed position.

23. A surgical navigation system according to claim 22, wherein the clamping arms are pivotable relative to each other.

24. A surgical navigation system according to claim 22, wherein the clamping arms each have a clamping surface, said clamping surfaces facing towards each other and at least one of said clamping surfaces carrying at least one tooth.

25. A surgical navigation system according to claim 24, wherein a stop device is provided for preventing the clamping surfaces from directly contacting each other in a closed position of the jaw part.

26. A surgical navigation system according to claim 22, wherein one of the two clamping arms is immovably or stationarily arranged on the shaft.

27. A surgical navigation system according to claim 22, wherein one of the two clamping arms is movably arranged on the shaft.

28. A surgical navigation system according to claim 14, wherein each of the applicator instruments has a handle arranged at a proximal end thereof for grasping the applicator instrument.

29. A surgical navigation system according to claim 28, wherein each of the applicator instruments has at least one actuating member which is coupled to at least one clamping arm in a movable manner in order to open or close the jaw part.

30. A surgical navigation system according to claim 14, wherein the bending angle of the applicator instrument is defined between the longitudinal axis and a stationary clamping arm of the jaw part.

31. A surgical navigation system according to claim 14, wherein the jaw part is designed in a form of forceps.

32. A surgical navigation system according to claim 14, the at least two applicator instruments further comprising at least one anchor element for anchoring the jaw part to a bone or in or on the cartilage defect.

33. A surgical navigation system according to claim 32, wherein the at least one anchor element is designed in a form of a spike.

34. A surgical navigation system according to claim 14, further comprising an insertion instrument which is insertable into a patient's body through the arthroscopic access and has a channel through which the applicator instruments are insertable into the patient's body.

35. A surgical navigation system according to claim 34, wherein the insertion instrument is designed in a form of an elongate sleeve defining the channel.

* * * * *